US00PP36063P2

(12) United States Plant Patent
Hung et al.

(10) Patent No.: US PP36,063 P2
(45) Date of Patent: Aug. 6, 2024

(54) ***MONSTERA* PLANT NAMED 'HUTAMT41'**

(50) Latin Name: *Monstera deliciosa*
Varietal Denomination: HUTAMT41

(71) Applicant: Huta Green Company Limited, Hanoi (VN)

(72) Inventors: Pham Ngoc Hung, Hiep Cuong Commune (VN); Le Tuan Anh, Thai Binh (VN)

(73) Assignee: Huta Green Company Limited, Hanoi (VN)

( * ) Notice: Subject to any disclaimer, the term of this patent is extended or adjusted under 35 U.S.C. 154(b) by 0 days.

(21) Appl. No.: 18/445,611

(22) Filed: Nov. 20, 2023

(51) Int. Cl.
*A01H 5/12* (2018.01)
*A01H 6/10* (2018.01)

(52) U.S. Cl.
USPC ..... Plt./373
CPC ..... *A01H 6/10* (2018.05)

(58) Field of Classification Search
USPC ..... Plt./373
CPC ..... A01H 5/12
See application file for complete search history.

*Primary Examiner* — Kent L Bell
(74) *Attorney, Agent, or Firm* — Samuel R. McCoy, Jr.

(57) ABSTRACT

'HUTAMT41' is a new and distinctive *Monstera* plant which is characterized by two distinct foliage colorations depending on ambient temperature at the time of leaf emergence and maturation, each with the same variegation pattern, borne on variegated petioles, and the stability of all characteristics from generation to generation. The new variety is typically produced as an indoor ornamental plant.

4 Drawing Sheets

Latin name of the genus and species: The Latin name of the genus and species of the novel variety disclosed herein is *Monstera deliciosa.*

Variety denomination: The inventive variety of *Monstera* disclosed herein has been given the variety denomination 'HUTAMT41'.

BACKGROUND OF THE INVENTION

Parentage: The claimed plant originated as a Ethyl methanesulfonate-induced, whole-plant mutation of an unnamed *Monstera deliciosa* plant that typified the species (not patented). In the spring of 2019, meristematic tissue culture propagation of said *Monstera deliciosa* plant was initiated at a plant tissue culture laboratory in Hanoi, Vietnam. After five months in culture, the plant tissue was transferred to an agar medium to induce multiplication of meristematic plant tissue. The plant tissue cultures which had developed juvenile leaf shoots and calluses, were treated with Ethyl methanesulfonate with the inventor's proprietary laboratory protocol. The treated plant tissue cultures then were rooted in soilless growing media. This process resulted in approximately 5000 rooted young plants. Said plants were grown to the four-true-leaf stage, at which point any plantlets exhibiting variation in leaf color, variation in leaf shape, or leaf variegation were isolated. In February of 2020, after evaluating said isolated plants, one plant was observed to exhibit unique foliage variegation relative to all other candidate plants resulting from the induced-mutation. The plant was isolated and further evaluated to confirm the characteristics first observed. In January of 2022, it was determined that the unique foliage variegation and coloration of the claimed plant would prove favorable for commercial marketability.

Asexual Reproduction: Asexual reproduction of 'HUTAMT41', by way of meristematic tissue culture propagation, was first performed in 2022 at a plant tissue culture laboratory in Hanoi, Vietnam. Three successive generations so produced have shown that the unique features of the instant cultivar are stable and reproduced true to type.

SUMMARY OF THE INVENTION

The cultivar 'HUTAMT41' has not been observed under all possible environmental conditions and the phenotype may vary somewhat with variations in the instant environment such as temperature, day length, and light intensity, without, however, any variance in genotype. The following characteristics have been repeatedly observed and represent the distinguishing characteristics of the new *Monstera* cultivar 'HUTAMT41'. These traits, in combination, distinguish 'HUTAMT41' as a new and distinct cultivar.

1. *Monstera* 'HUTAMT41' exhibits cordate leaves that are strongly incised and fenestrated; and
2. *Monstera* 'HUTAMT41' exhibits variegated petioles that vary from yellow-green with green-yellow irregular longitudinal stripes to green-yellow with yellow-green irregular longitudinal stripes; and
3. *Monstera* 'HUTAMT41' exhibits foliage that, when grown at ambient temperatures below or near 30 degrees Celsius, is dark green and irregularly flecked and blotched with a near-white coloration; and
4. *Monstera* 'HUTAMT41' exhibits foliage that, when grown at ambient temperatures near or above 35 degrees Celsius, is lighter green and irregularly flecked and blotched with a lighter shade of yellow-green, nearer to yellow; and
5. *Monstera* 'HUTAMT41' exhibits stable foliage coloration that does not fade if moved from lower to higher ambient temperatures or darken when moved from higher to lower ambient temperatures.

BRIEF DESCRIPTION OF THE FIGURES

The photographs were taken using conventional techniques and although colors may appear different from actual colors due to light reflectance it is as accurate as possible by conventional photographic techniques.

BOTANICAL DESCRIPTION OF THE PLANT

Figure 1:
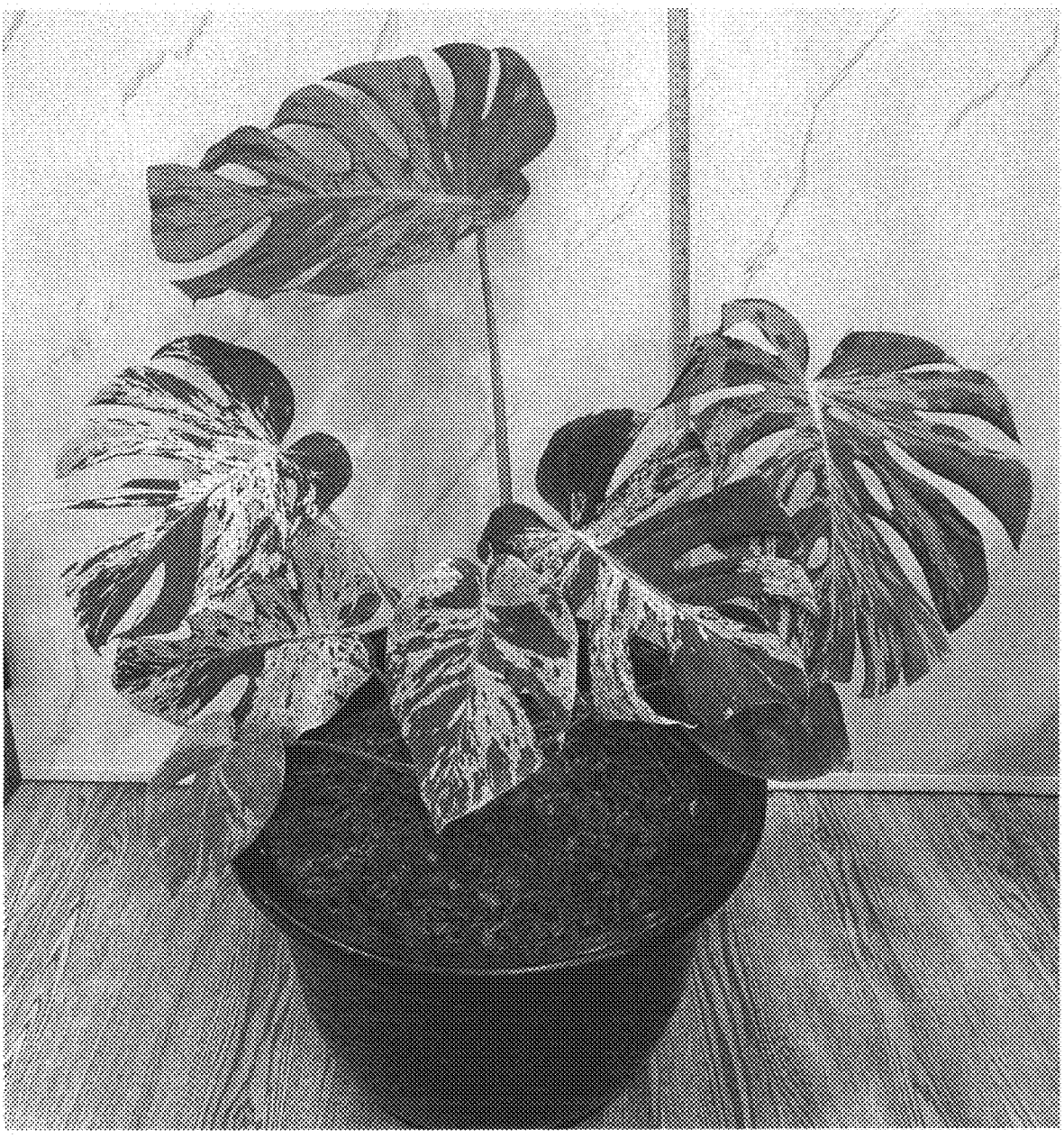
FIG. 1 shows, as nearly true as it is reasonably possible to make the same in color illustrations of this type, an exemplary plant of the new cultivar, 'HUTAMT41'. The plant shown is approximately 9 months old from a rooted cutting, potted into a 25 cm nursery container, grown in a greenhouse in Hanoi, Vietnam. The plant was first grown in a climate-controlled greenhouse before subsequently being moved outdoors.
Figure 2:
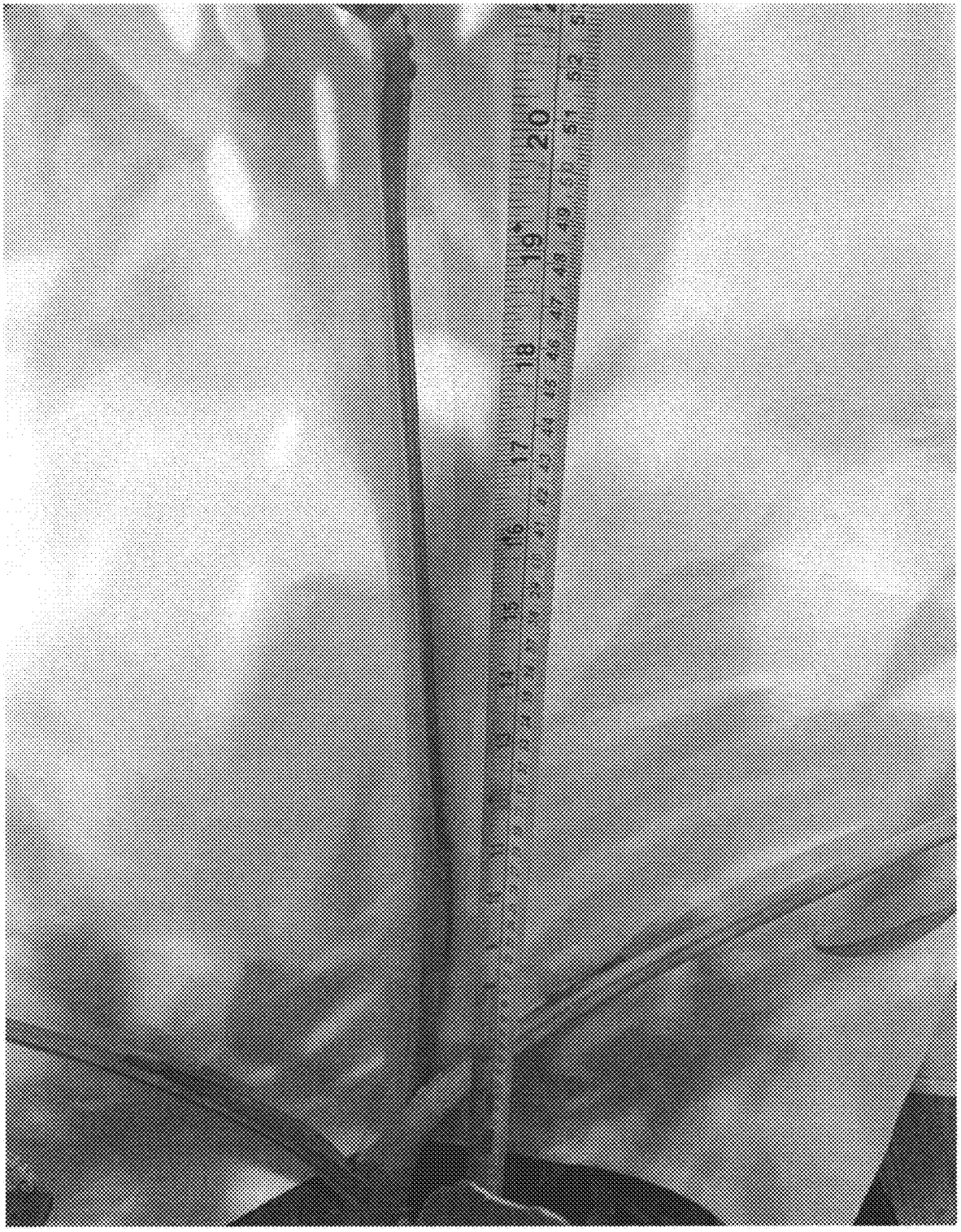
FIG. 2 illustrates the petioles of 'HUTAMT41'.
Figure 3:
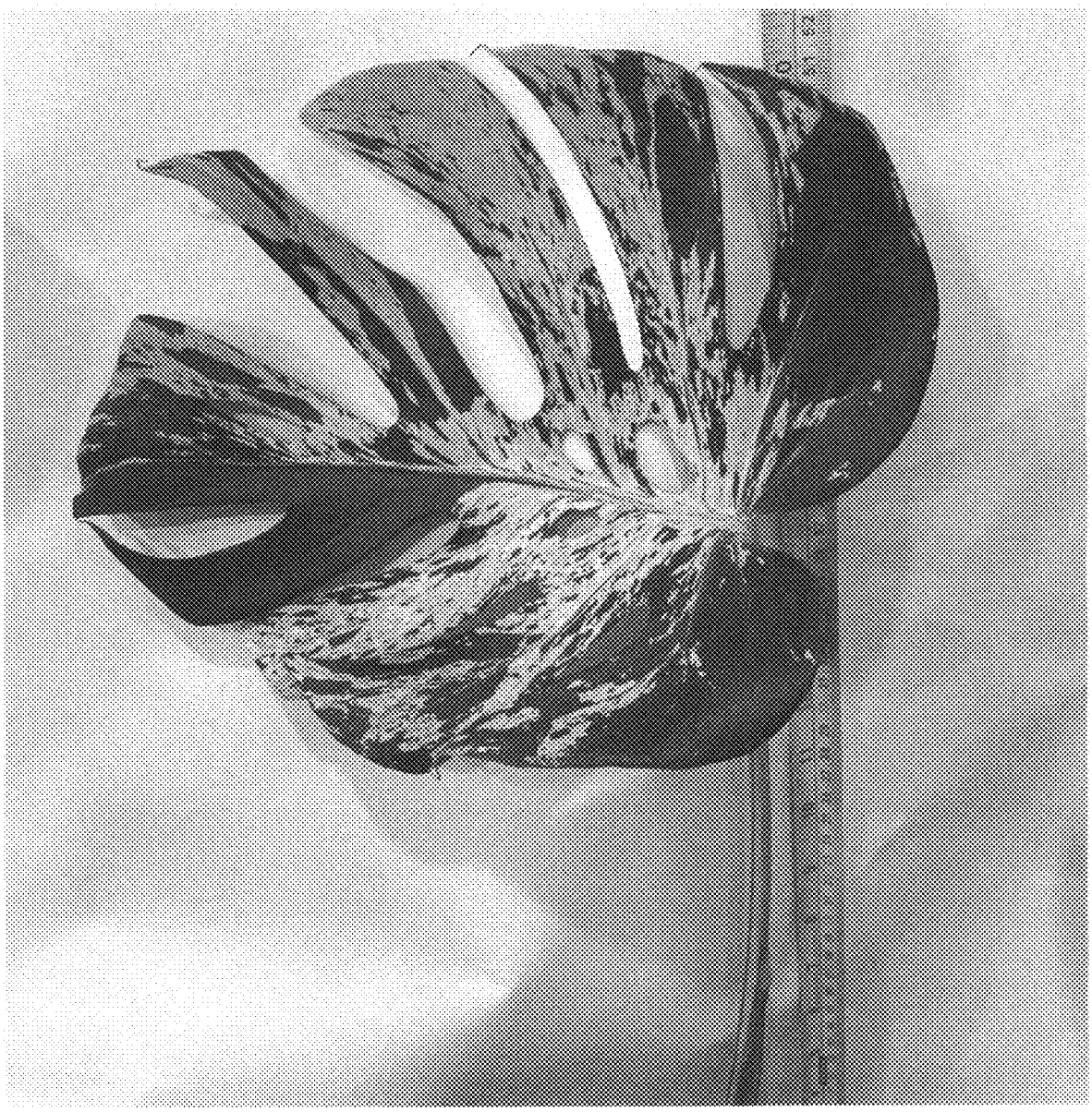
FIG. 3 illustrates the coloration of the mature foliage of 'HUTAMT41' when grown in a climate-controlled greenhouse, in ambient temperatures below 30 degrees Celsius.
Figure 4:
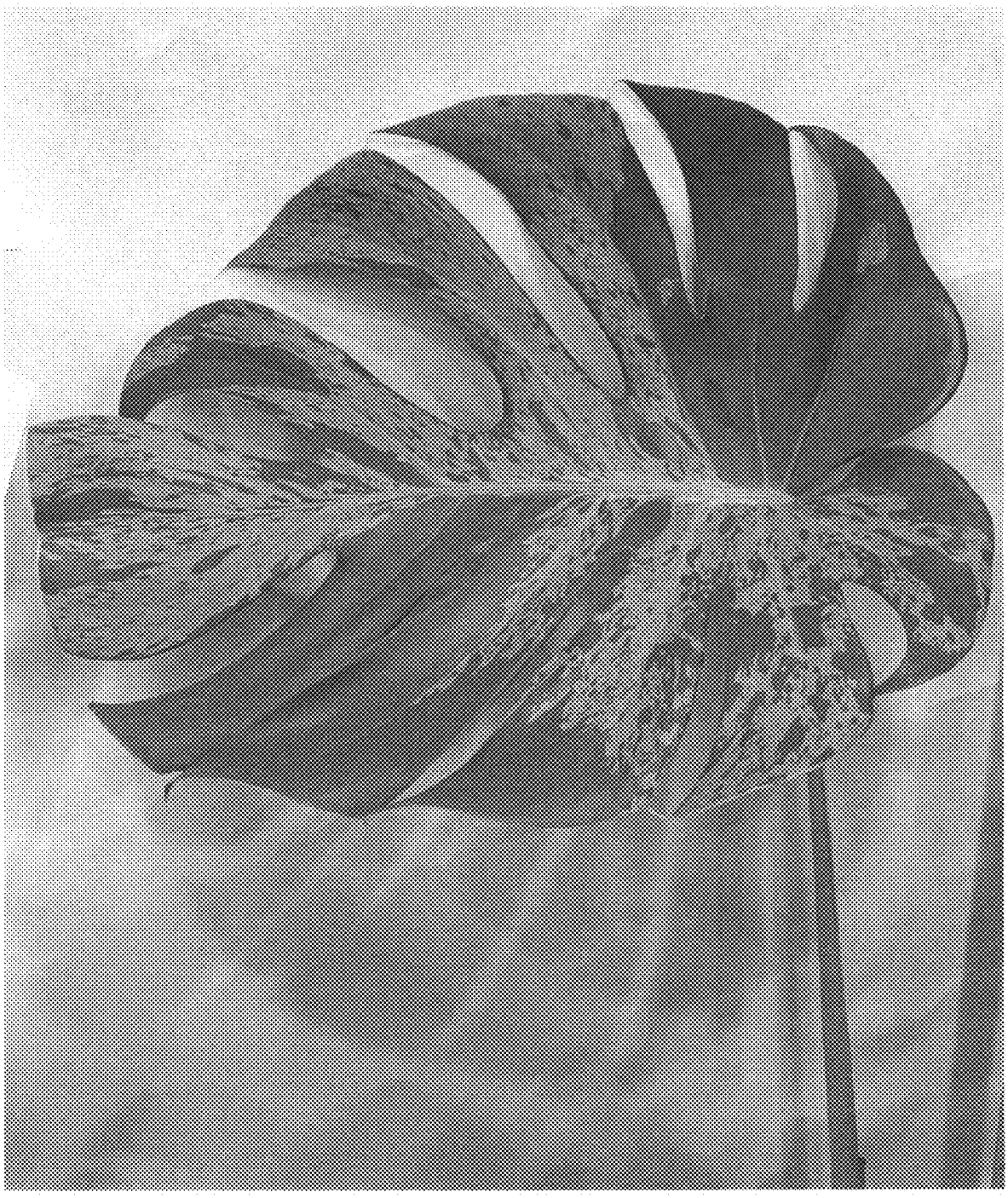
FIG. 4 illustrates the illustrates the coloration of the mature foliage of 'HUTAMT41' when grown outdoors, in ambient temperatures above 35 degrees Celsius.

The following observations and measurements made in October of 2023 describe a 9-month-old 'HUTAMT41' plant grown in a 25 cm nursery container at commercial greenhouse in Hanoi, Vietnam. Plants were produced using conventional greenhouse production protocols for *Monstera* species which consisted of overhead irrigation twice a week, weekly applications of a liquid 20-20-20 fertilizer at an electroconductivity of 0.8, and anti-bacteria oxalinic acid at a rate of 375 parts-per-million and Imidacloprid insecticide at a rate 100 parts-per-million applied every two weeks. Plants were initially grown under shade (ranging from 5,000 to 15,000 lux) with ambient temperatures ranging from 20 to 30 degrees Celsius and humidity levels ranging from 70 to 80 percent and then later moved outdoors to higher light levels (60,000 lux) and temperatures ranging from 35 to 40 degrees Celsius.

Those skilled in the art will appreciate that certain characteristics will vary with older or, conversely, with younger plants. 'HUTAMT41' has not been observed under all possible environmental conditions. Where dimensions, sizes, colors and other characteristics are given, it is to be understood that such measurements are approximations or averages set forth as accurately as practicable. The phenotype of the variety may differ from the descriptions set forth herein with variations in environmental, climatic, and cultural conditions. Color notations are based on The Royal Horticultural Society Colour Chart, The Royal Horticultural Society, London, second edition.

A botanical description of 'HUTAMT41' and comparisons with the parent and the most similar variety of common knowledge are provided below.

General plant description:

*Growth habit.*—Monopodial evergreen perennial; plants will eventually develop a stem with age.

*Plant profile.*—Upright, globular.

*Height.*—Approximately 53 cm.

*Width.*—Approximately 50 cm.

*Plant vigor.*—Moderately vigorous.

*Propagation.*—Method — Meristematic tissue culture. Time to initiate roots — Approximately 26 weeks to initiate roots at an average ambient temperature of 25 degrees Celsius. Crop time — Approximately 16 weeks to produce a well-rooted, marketable 30 cm container from a rooted cutting.

*Environmental tolerances.*—Moderately high tolerance to rain; low to moderate tolerance to wind; not drought tolerant; tolerant of temperatures to at least 35 degrees Celsius. Cold hardy to USDA Hardiness Zone 10.

*Pest resistance and susceptibility.*—Plants have not been observed to be any more or less susceptible or resistant to pathogens and pests common to *Monstera* sp.

Root system:

*General.*—*Monstera* sp. has the propensity to produce both subterranean and aerial roots.

*Branching.*—Freely branched.

*Density.*—Moderately dense.

*Distribution.*—Subterranean roots are shallow to moderately deep.

*Texture.*—Fleshy; smooth; aerial roots lack root hairs while subterranean roots are bare root hairs.

Stems:

*Branching characteristics.*—*Monstera* sp. is a monopodial plant; plants eventually develop a stem with age. However, to date, no stems have developed on the claimed plant.

Foliage:

*Arrangement.*—Alternate to spiraled.

*Division.*—Simple.

*Attachment.*—Petiolate.

*Quantity of leaves per shoot.*—1.

*Quantity of shoots per plant.*—8.

*Quantity of leaves per plant.*—8.

*Lamina.*—Shape — Cordate; laminas become progressively pinnatifid and fenestrated with age. Apex — Broadly acuminate. Base — Cordate. Aspect — Convex; laminar lobes are pendulous. Attitude — Outward to somewhat pendulous, at an approximate angle of 90 degrees to the petiole. Dimensions — 26.5 cm long and 21.5 cm wide. Margin — Juvenile foliar margins are entire with light, coarse undulation. Mature foliar margins are incised, lobed, and fenestrated. Texture and luster, adaxial surface — Smooth, glabrous, and slightly to moderately glossy. Texture and luster, abaxial surface — Smooth, glabrous, and slightly glossy to matte. Juvenile color, adaxial surface — Two distinct colorations may be present, each coloration being dependent on ambient temperature at the time of leaf emergence, and each with the same variegation pattern. When foliage emerges at ambient temperatures below or near 30 degrees Celsius, the foliage is dark green, nearest to RHS 139A, and irregularly flecked and blotched with a combination of white, RHS 155A, and green-white, RHS 157A, though predominantly white, RHS 155A. Additionally, these areas of flecking and blotching are themselves flecked with dark green, RHS 139A. The coloration of this foliage will not fade if subjected to higher ambient temperatures once it has emerged. When foliage emerges at ambient temperatures above or near 35 degrees Celsius, the foliage is a lighter shade of green, nearest to in between RHS 141A and 143A, and irregularly flecked and blotched with yellow-green, RHS 150B. These areas of flecking and blotching are themselves flecked with yellow-green, nearest to RHS 141B. The coloration of this foliage will not change if subjected to lower ambient temperatures once it has emerged. Juvenile color, abaxial surface — Two distinct colorations may be present, each coloration being dependent on ambient temperature at the time of leaf emergence, and each with the same variegation pattern. When foliage emerges at ambient temperatures below or near 30 degrees Celsius, the foliage is yellow-green, nearest to a mixture of RHS 144A and 144B, and irregularly flecked and blotched with a combination of green-white, RHS 157B, and yellow-green, RHS 145D, though predominantly green-white, RHS 157B. Additionally, these areas of flecking and blotching are themselves flecked with yellow-green, nearest to a mixture of RHS 144A and 144B. The coloration of this foliage will not fade if subjected to higher ambient temperatures once it has emerged. When foliage emerges at ambient temperatures above or near 35 degrees Celsius, the foliage is yellow-green, nearest to RHS 144B, and irregularly flecked and blotched with yellow-green, RHS 145C. These areas of flecking and blotching are themselves flecked with yellow-green, nearest to RHS 144B. The coloration of this foliage will not change if subjected to lower ambient temperatures once it has emerged. Mature color, adaxial surface — Two distinct colorations may be present, each coloration being dependent on ambient temperature during foliage maturation, and each with the same variegation pattern. When foliage emerges at ambient temperatures below or near 30 degrees Celsius, the foliage is dark green, nearest to RHS 139A, and irregularly flecked and blotched with a combination of white, RHS 155A, and green-white, RHS 157A, though predominantly white, RHS 155A. Additionally, these areas of flecking and blotching are themselves flecked with dark green, RHS 139A. The coloration of this foliage will not fade if subjected to higher ambient temperatures once it has emerged. When foliage emerges at ambient temperatures above or near 35 degrees Celsius, the foliage is a lighter shade of green, nearest to in between RHS 141A and 143A, and irregularly flecked and blotched with yellow-green, RHS 150B. These areas of flecking and blotching are themselves flecked with yellow-green, nearest to RHS 141B. The coloration of this foliage will not change if subjected to lower ambient temperatures once it has emerged. Mature color, abaxial surface — Two distinct colorations may be present, each coloration being dependent on ambient temperature during foliage maturation, and each with the same variegation pattern. When foliage matures at ambient temperatures below or near 30 degrees Celsius, the foliage is yellow-green, nearest to a mixture of RHS 144A and 144B, and irregularly flecked and blotched with a combination of green-white, RHS 157B, and yellow-green, RHS 145D, though predominantly green-white, RHS 157B. Additionally, these areas of flecking and blotching are themselves flecked with yellow-green, nearest to a mixture of RHS 144A and 144B. The coloration of this foliage will not fade if subjected to higher ambient temperatures. When foliage matures at ambient temperatures above or near 35 degrees Celsius, the foliage is yellow-green, nearest to RHS 144B, and irregularly flecked and blotched with yellow-green, RHS 145C. These areas of flecking and blotching are themselves flecked with yellow-green, nearest to RHS 144B. The coloration of this foliage will not change if subjected to lower ambient temperatures. Venation — Vein pattern — Pinnate. Vein color, adaxial surface — When foliage emerges and matures at ambient temperatures below or near 30 degrees Celsius, the main veins are white, RHS 155A, and flecked and streaked with green, nearest to RHS 137A. Lateral veins are either indistinguishable from the surrounding foliage or green, RHS 137A. When foliage emerges and matures at ambient temperatures above or near 35 degrees Celsius, the main veins are yellow-green, RHS 150C, and flecked and streaked with yellow-green, nearest to RHS 144C. Lateral veins are either indistinguishable from the surrounding foliage or yellow-green, RHS 144C. Vein color, abaxial surface — When foliage emerges and matures at ambient temperatures below or near 30 degrees Celsius, the main veins and lateral veins are yellow-green, nearest to RHS 145C, and occasionally flecked or suffused with yellow-green, nearest to RHS 145A. When foliage emerges and matures at ambient temperatures above or near 35 degrees Celsius, the main veins and lateral veins are yellow-green, nearest to RHS 145C, and occasionally flecked or suffused with yellow-green, nearest to RHS 144C.

*Petiole.*—Attachment — Sheathed. Aspect — Terete to subterete proximally and becoming semi-terete at the geniculum. Length — Approximately 25.4 cm. Width — Approximately 3.8 cm, including the petiole wings, at the proximal end and 1.25 cm at the distal end. Strength — Moderately strong. Texture — Glabrous. Luster — Matte to very slightly glossy. Color, adaxial surface — Varying from yellow-green (RHS 145A) with green-yellow irregular longitudinal stripes (RHS 1B) to green-yellow (RHS 1B) with yellow-green irregular longitudinal stripes (RHS 145A). Color, abaxial surface — Varying from yellow-green (RHS 145A) with green-yellow irregular longitudinal stripes (RHS 1B) to green-yellow (RHS 1B) with yellow-green irregular longitudinal stripes (RHS 145A). Geniculum — Length — 1.8 cm. Diameter — 0.7 cm. Aspect — Semi-terete, with genicular wings running along the length of the margins. Genicular wings — Dimensions — 1.8 cm long and 0.3 cm wide. Aspect — Strongly undulate. Color — Yellow-green, RHS 145B. Texture and luster — Matte to very slightly glossy. Color, excluding genicular wings. Color, adaxial surface — Yellow-green, RHS 145A. Color, abaxial surface — Yellow-green, RHS 145B. Petiole wings — General Description — Two petiole wings are present at the base of each petiole. Length — Approximately 7.6 cm. Width — Approximately 1.25 cm at the base. Margins — Entire; involute; lightly undulated. Texture and luster — Glabrous and very slightly glossy. Color, adaxial surface — Yellow-green, nearest to RHS 144C, and occasionally striped or strongly suffused with green-yellow, RHS 1B. Color, abaxial surface — Yellow-green, nearest to RHS 144C, and occasionally striped or strongly suffused with green-yellow, RHS 1B.

Inflorescence: *Monstera deliciosa* typically produces a spathe and spadix inflorescence, but no flowering of the claimed plant has been observed to date.

Flower buds: No flowering has been observed to date.

Flowers: No flowering has been observed to date.

Reproductive organs: No flowering has been observed to date.

Seed and fruit: Seed production has not been observed.

Comparisons with the parent: Plants of the new cultivar 'HUTAMT41' may be distinguished from the parent, an unnamed *Monstera deliciosa* plant that typified the species (not patented), by the characteristics described in Table 1.

TABLE 1

| Characteristic | 'HUTAMT41' | The parent |
|---|---|---|
| Petiole coloration. | Varying from yellow-green with green-yellow irregular longitudinal stripes to green-yellow with yellow-green irregular longitudinal stripes. | Solid green. |
| Foliage coloration. | Two distinct colorations may be present, each coloration being dependent on light exposure at the time of leaf emergence, and each with the same variegation pattern: dark green and irregularly flecked and blotched with near-white when grown under low light; and, a lighter shade of green that is irregularly flecked and blotched with a light yellow-green, nearer to yellow. | Solid green. |
| Vein coloration. | When grown under low light, the main veins are white and flecked and streaked with green. Lateral veins are either indistinguishable from the surrounding foliage or green. When grown under high light, the main veins are yellow-green and flecked and streaked with a darker shade of yellow-green. Lateral veins are either indistinguishable from the surrounding foliage or a lighter shade of yellow-green. | Light yellow-green. |

Comparisons with the most similar commercial variety: Plants of the new cultivar 'HUTAMT41' may be distinguished from the most similar commercial comparator known to the inventor, *Monstera deliciosa* 'Thai Constellation' (not patented), by the characteristics described in Table 2.

TABLE 2

| Characteristic | 'HUTAMT41' | 'Thai Constellation' |
|---|---|---|
| Plant height. | Taller than 'Thai Constellation'. | Shorter than 'HUTAMT41'. |
| Petiole coloration. | Varying from yellow-green with green-yellow irregular longitudinal stripes to green-yellow with yellow-green irregular longitudinal stripes. | Green or green and white variegated. |
| Lamina shape. | Cordate, with a length-to-width ratio of 1.2 to 1.5. | Broadly cordate, with a length-to-width ratio of 1 to 1.2 |
| Degree of leaf incisions. | More deeply incised than 'Thai Constellation'. | Less incised relative to 'HUTAMT41'. |
| Expression of the foliar color patterns. | Two distinct colorations may be present, each coloration being dependent on light exposure at the time of leaf emergence, and each with the same variegation pattern: dark green and irregularly flecked and blotched with near-white when grown under low light; and, a lighter shade of green that is irregularly flecked and blotched with a light yellow-green, nearer to yellow. | Mid to dark green with white or pale-yellow flecks and blotches. |

That which is claimed is:

1. A new and distinct variety of *Monstera deliciosa* plant named 'HUTAMT41', substantially as described and illustrated herein.

* * * * *